US009816075B2

(12) United States Patent
MacDonnell et al.

(10) Patent No.: US 9,816,075 B2
(45) Date of Patent: *Nov. 14, 2017

(54) COMPOUNDS WITH MODIFYING ACTIVITY ENHANCED UNDER HYPOXIC CONDITIONS

(71) Applicant: Board of Regents, The University of Texas System, Austin, TX (US)

(72) Inventors: Frederick M. MacDonnell, Arlington, VA (US); Thamara K. Janaratne, San Diego, CA (US); Sanjay Awashti, Arlington, VA (US)

(73) Assignee: Board of Regents, The University of Texas System, Austin, TX (US)

( * ) Notice: Subject to any disclaimer, the term of this patent is extended or adjusted under 35 U.S.C. 154(b) by 213 days.

This patent is subject to a terminal disclaimer.

(21) Appl. No.: 14/531,774

(22) Filed: Nov. 3, 2014

(65) Prior Publication Data
US 2015/0152390 A1 Jun. 4, 2015

Related U.S. Application Data

(62) Division of application No. 13/564,169, filed on Aug. 1, 2012, now Pat. No. 8,877,215, which is a division of application No. 11/496,837, filed on Aug. 1, 2006, now Pat. No. 8,246,967.

(60) Provisional application No. 60/704,613, filed on Aug. 2, 2005.

(51) Int. Cl.
*A61K 9/00* (2006.01)
*C12N 5/09* (2010.01)
*C07F 15/00* (2006.01)
*A61K 31/435* (2006.01)
*A61K 49/00* (2006.01)

(52) U.S. Cl.
CPC ........ *C12N 5/0693* (2013.01); *C07F 15/0046* (2013.01); *C07F 15/0053* (2013.01); *A61K 31/435* (2013.01); *A61K 49/0017* (2013.01); *C12N 2500/10* (2013.01)

(58) Field of Classification Search
None
See application file for complete search history.

(56) References Cited

U.S. PATENT DOCUMENTS 4,721,669 A   1/1988   Barton
5,171,853 A  12/1992   Thorp et al.

OTHER PUBLICATIONS

Townsend et al. "The importance of glutathione in human disease", Biomedicine & Pharmacotherapy, 57:145-155 (2003).
Gupta et al. "[RuO(dppz)(tpy)]2+: a DNA Cleavage Agent with High DNA Affinity", Chem Int Ed Engl, 31 (8):1048-1050 (1992).
Liu et al. "Synthesis, Characterization and Antitumor Activity of a Series of Polypyridyl Complexes", Metal Based Drugs, 7(6):343-348 (2000).
Bolger et al. "Mononuclear and Binuclear Tetrapyrido[3,2-a:2',3'-c:3",2'-h:2"',3"'-j]phenazine (tpphz) Ruthenium and Osmium Complexes", Inorg Chem, 35:2937-2944 (1996).
Grover et al. "Studies of Electrocatalytic DNA Cleavage by Oxoruthenium(IV).", Inorg Chem, 31:2014-2020 (1992).
Friedman et al. "Molecular "Light Switch" for DNA: Ru(bpy)2(dppz)2+", J Am Chem Soc, 112:4960-4962 (1990).
Williams et al. "Hypoxia and oxidative stress in breast cancer Tumor hypoxia—therapeutic considerations", Breast Cancer Res, 3:328-331 (2001).
Konduri et al. "Ruthenium Photocatalysts Capable of Reversibly Storing up to Four Electrons in a Single Acceptor Ligand: A Step Closer to Artificial Photosynthesis", Angew Chem Int Ed, 41(17):3185-3187 (2002).
Brown, Martin J. "Hypoxic cytotoxic agents: a new approach to cancer chemotherapy", Drug Resistance Updates, 3:7-13 (2000).
Bush et al. "Definitive Evidence for Hypoxic Cells Influencing Cure in Cancer Therapy", Br J Cancer, 37: Suppl 3:302-306 (1978).
Gatenby et al. "Oxygen Distribution in Squamous Cell Carcinoma Mteastases and It's Relationship to Outcome of Radiation Therapy", Int J Radiation Oncology Biol Phys, 14(5):831-838 (1988).
Haffty et al. "Bioreductive Alkylating Agent Porfiromycin in Combination With Radiation Therapy for the Management of Squamous Cell Carcinoma of the Head and Neck", Rad Onc Inv, 5:235-245 (1997).
Hockel et al. "Intratumoral pO2 predicts survival in advanced cancer of the uterine cervix", Radiotherapy and Oncology, 26:45-50 (1993).
De Tacconi et al. "Infiuice of pH on the Photochemical and Electrochemical Reduction of the Dinuclear Ruthenium Complex, [(phen)2Ru(tatpp)Ru(phen)2]Cl4, in Water", Chem Eur J, 12 pp (2005).

(Continued)

*Primary Examiner* — Michael G Hartley
*Assistant Examiner* — Melissa Perreira
(74) *Attorney, Agent, or Firm* — Mickki D. Murray; Parks IP Law LLC

(57) ABSTRACT

Compositions and methods for modifying one or more biologic targets are provided. Suitable targets include cells, DNA, proteins, enzymes, and/or a subject in need thereof. The compositions may exist as a monomer or multimer and are active in a biologic environment with enhanced activity in hypoxic environments and, thus, exhibit improved specificity for hypoxic biologic targets (e.g., tumorigenic cells and those undergoing uncontrolled cell growth). A composition typically comprises a complex with an overall charge of 2+ or greater having at least one ruthenium atom attached to a redox active ligand. The redox active ligand helps maintain separation of more than one ruthenium atom. Suitable compositions may further include a terminal ligand comprising a heterocyclic aromatic compound. When provided to a biologic target, the composition modifies the biologic target and no additional compounds need be provided. Suitable compositions are typically catalytic and regenerative in the presence of a reducing agent.

20 Claims, 10 Drawing Sheets

(56) References Cited

OTHER PUBLICATIONS

Erkkila et al. "Recognition and Reaction of Metallointercalators with DNA", Chem Rev, 99:2777-2795 (1999).

Fu et al. "DNA Cleavage by Photogenerated Rh2(O2CCH3)4(H20)2+", Inorg Chem, 40:2476-2477 (2001).

Fu et al. "DNA Photocleavage by a Supramolecular Ru(II)—Viologen Complex", Inorg Chem, 41:3808-3810 (2002).

Greco et al. "How to Overcome (and Exploit) Tumor Hypoxia for Targeted Gene Therapy", J Cellular Phys, 197:312-325 (2003).

Gupta et al. "Synthesis and Properties of New DNA Cleavage Agents Based on Oxoruthenium(IV)", Inorg Chem, 32:310-316 (1993).

Holder et al. "Design Aspects for the Development of Mixed-Metal Supramolecular Complexes Capable of Visible Light Induced Photocleavage of DNA", Inorg Chem, 43:303-308 (2004).

Konduri et al. "Multielectron Photoreduction of a Bridged Ruthenium Dimer, [(phen)2Ru(tatpp)Ru(phen)2][PF6]4: Aqueous Reactivity and Chemical Spectroelectrochemical Identification of the Photoproducts", J Am Chem Soc, 126:11621-11629 (2004).

Lee et al. "Hypoxia-Dependent Retinal Toxicity of Bioreductive Anticancer Prodrugs in Mice", Toxic Appl Pharma, 163:50-59 (2000).

Patterson et al. "AQ4N: a new approach to hypoxia-activated cancer chemotherapy", British J Cancer, 83 (2):1589-1593 (2000).

Rauth et al. "Bioreductive Therapies: An Overview of Drugs and Their Mechanisms of Action", Int J Radiation Oncology Biol Phys, 42(4):755-762 (1998).

Rischin et al. "Phase I Trial of Concurrent Tirapazamine, Cisplatin, and Radiotherapy in Patients With Advanced Head and Neck Cancer", J Clinical Oncology, 19(2):535-542 (2001).

Rofstad et al. "Hypoxia-induced metastasis of human melanoma cells: involvement of vascular endothelial growth factor-mediated angiogenesis", British J Cancer, 80(11) 1697-1707 (1999).

Van Pawel et al. "Tirapazamine Plus Cisplatin Versus Cisplatin in Advanced Non-Small-Cell Lung Cancer: A Report of the International CATAPULT I Study Group", J Clinical Oncology, 18(6):1351-1359 (2000).

Absalon et al. "Sequence-Specific Double-Strand Cleavage of DNA by Fe-Bleomycin", Biochemistry, 34:2065-2075 (1995).

Benites et al. "Metal-Ligand Charge-Transfer-Promoted Photoelectronic Bergman Cyclization of Copper Metalloenediynes", J Am Chem Soc, 125:6434-6446 (2003).

Bradley et al. "Direct DNA Photocleavage by a New Intercalating Dirhodium (II/II) Complex", Inorg Chem, 43:2450-2452 (2004).

Che et al. "Platinum(II) Complexes of Dipyridophenazine as Metallointercalators for DNA and Potent Cytotoxic Agents against Carcinoma Cell Lines", 1999.

Coleman et al. "Chemical Modifiers of Cancer Treatment", J Clinical Oncology, 6(4):709-733 (1988).

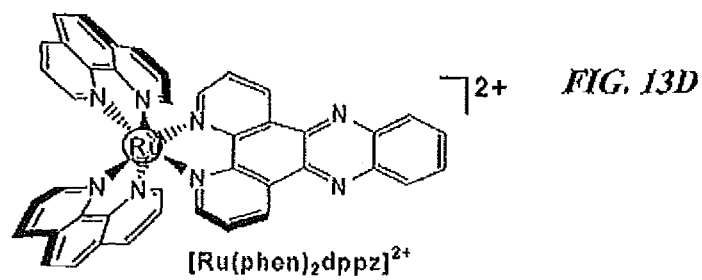
*FIG. 13D*
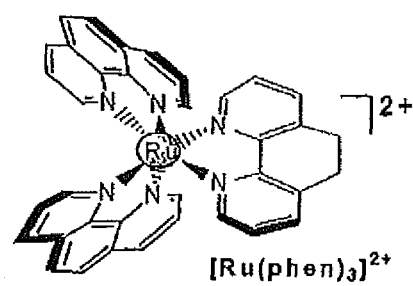
*FIG. 13E*
*FIG. 18*
|              | 1 | 2 | 3 | 4 | 5 | 6 | 7  | 8  | 9  | 10 |
|--------------|---|---|---|---|---|---|----|----|----|----|
| pH           | 6 | 6 | 6 | 7 | 7 | 8 | 10 | 11 | 11 | 11 |
| P            | - | - | + | - | + | + | +  | -  | -  | +  |
| GSH(20 eq)   | - | + | + | + | + | + | +  | -  | +  | +  |

# COMPOUNDS WITH MODIFYING ACTIVITY ENHANCED UNDER HYPOXIC CONDITIONS

CROSS-REFERENCES TO RELATED APPLICATIONS

This application is a divisional of Ser. No. 13/564,169 filed on Aug. 1, 2012 which issued as U.S. Pat. No. 8,877,215 and which is a divisional of Ser. No. 11/496,837, filed on Aug. 1, 2006 and issued as U.S. Pat. No. 8,246,967 and which claims benefit of Ser. No. 60/704,613 filed on Aug. 2, 2005.

STATEMENT REGARDING FEDERALLY SPONSORED RESEARCH OR DEVELOPMENT

Not applicable.

BACKGROUND OF THE INVENTION

The invention relates generally to compounds with cell modifying activity and, in particular, to those with modifying activity also suitable under hypoxic conditions.

Current therapies directed against cells with uncontrolled growth properties (e.g., high proliferating cells, cancerous cells and tumors) require that they include a set of unique criteria in order to avoid damaging normal growing and/or nonproliferating cells. Such criteria include an ability to activate toxic compounds as well as a preferential action under low oxygen microenvironments in which most solid tumors exist. The latter is particularly important because it has been found that hypoxic subpopulations of cells exist in solid tumors that are directly linked with negative outcomes, such as a resistance to radiotherapy, resistance to a number of forms of chemotherapy, stimulation of metastasis, as examples.

Unfortunately, current therapies are generally lacking and few agents work better under hypoxic conditions than normal conditions. Accordingly, there remains a need for compounds with activity on biologic targets, especially compounds with activity under more hypoxic conditions. In addition, there remains a need for such compounds with suitable activity against targets, such as cells with uncontrolled growth properties, and with chemotherapeutic activity. A considerable therapeutic benefit would be achieved if such compounds were available, and could be combined with other treatments, to reduce or eliminate toxic portions of these biologic targets, such as cancerous cells and tumors.

SUMMARY OF THE INVENTION

The invention described herein solves problems associated with current therapies directed against biologic targets, such as DNA, enzymes, cells undergoing uncontrolled growth, and subjects in need thereof, by providing methods and compositions with improved biologic modifying activity, capable of targeting DNA, enzymes and cells, including those in a subject in need thereof. The improved activity is enhanced in hypoxic environments enabling such methods and compositions to work in such environments and on biologic targets provided under more hypoxic environments. With compositions and methods described herein, biologic targets in non-hypoxic environments remain unaffected.

Generally, and in one form, one or more compositions are provided, each composition comprising one or more stereoisomers and their derivatives, each comprising at least one ruthenium atom attached to a ligand that is redox active. The composition typically has an overall charge of 2+ or greater and exhibits modifying activity on one or more biologic targets (e.g., nucleic acid, enzyme, one or more cancerous cells undergoing uncontrolled growth). No additional agents need be provided for the modifications described herein. In addition, said compositions may reductively regenerate. The composition may be paramagnetic, catalytic and regenerative in the presence of a reducing agent as well as a diradical.

In another form, a method for modifying a biologic target is provided. The method comprising providing a complex to the biologic target, the complex having at least one ruthenium atom attached to a redox active ligand and modifying the biologic target. No additional compounds need be provided for the method described herein. The biologic target may include DNA, hypoxic cell, and/or a replication enzyme as well as a subject having the suitable biologic target. The method may further include adding a pharmaceutical carrier to the complex as well as administering the complex to a subject in need thereof. The complex is often active in the presence of a reducing agent and is catalytic.

The complex may further comprise a terminal ligand that has a heterocyclic aromatic compound, such as a pyridine, pyrimidine, ethylenediamine, 1,10-phenanthroline, 2,2'-bipyridine, 1,10-phenanthroline-5,6-dione, and derivatives thereof. The complex may be a dinuclear ruthenium complex including $[Ru_2(X)_4tatpp]^{4+}$, $[Ru_2(X)_4tatpq]^{4+}$, $[Ru_2(X)_4tpphz]^{4+}$, and their salts, stereoisomers and derivatives thereof, wherein X includes pyridine, pyrimidine, ethylenediamine, 1,10-phenanthroline, 2,2'-bipyridine, 1,10-phenanthroline-5,6-dione, and derivatives thereof.

In yet another form, a complex may comprises at least one ruthenium atom possessing a first ligand that is an heterocyclic aromatic compound attached to a second ligand that is redox active. The complex is capable of modifying the biologic target in a hypoxic environment. Modifications include breaking one strand of DNA, breaking two strands of DNA in close proximity, inhibiting topoisomerase I, inhibiting topoisomerase II, inhibiting impulse transmission, promoting cellular apoptosis, inhibiting cell proliferation, inhibiting cell growth, inhibiting DNA replication, inhibiting DNA duplication, inhibiting tumor progression, inhibiting tumor growth, and combinations, thereof. The second ligand further comprises 9,11,20,22-tetraazatetrapyrido[3,2-a:2',3'-c:3",2"-l: 2''',3'''-n]-pentacerte, 9,11,20,22-tetraazatetrapyrido[3,2-a:2',3'-c:3",2"-l:2''',3'''-n]-pentacene-10,21-quinone), tetrapytido[3,2-a:2',3'-c:3",2"-h:2''',3'''-j]phenazine), and dipyrido[3,2-a:2',3'-c]phenazine and derivatives thereof. The first ligand further comprises pyridine, pyrimidine, ethylenediamine, 1,10-phenanthroline, 2,2'-bipyridine, 1,10-phenanthroline-5,6-dione and derivatives thereof. The method may further comprise administering the complex to a mammal in need thereof.

In still another form, a complex may be provided with a suitable carrier wherein the complex has an overall charge of 2+ or greater and comprises at least one ruthenium atom possessing a first ligand that is an heterocyclic aromatic compound attached to a second ligand that is redox active. Such a complex with a suitable carrier may be provided to a biologic target as well as to a subject in need thereof. Typically, the first ligand is a heterocyclic aromatic compound and the second ligand provides a low lying triplet excited state to the composition upon reduction.

Those skilled in the art will further appreciate the above-noted features and advantages of the invention together with other important aspects thereof upon reading the detailed description that follows in conjunction with the drawings.

BRIEF DESCRIPTION OF SEVERAL VIEWS OF THE DRAWINGS

For a more complete understanding of the features and advantages of the present invention, reference is now made to the detailed description of the invention along with the accompanying figures in which corresponding numerals in the different figures refer to corresponding parts and in which:

FIGS. 13A to 13E depicts reduction schematics of several representative compositions;

FIG. 18 depicts DNA modifying activity of a suitable composition in varying pH conditions;

DETAILED DESCRIPTION

Figure 1:
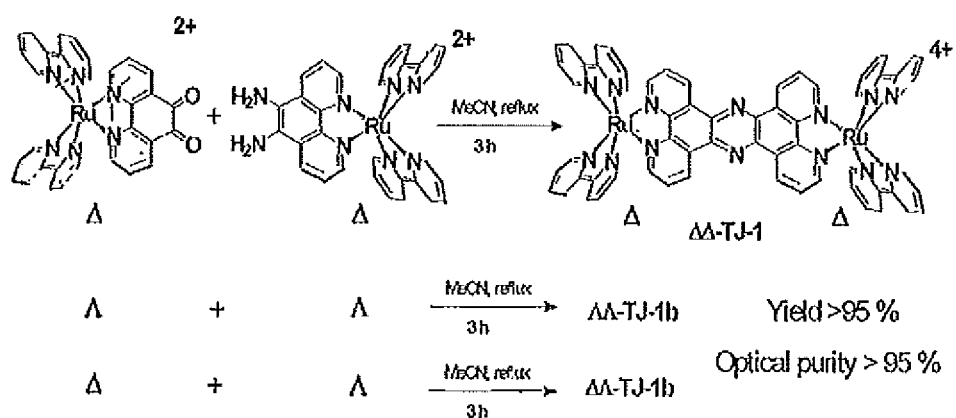
FIG. 1 depicts a schematic of a stereospecific synthetic route for preparation of one or more suitable compositions.

Although making and using various embodiments of the present invention are discussed in detail below, it should be appreciated that the present invention provides many inventive concepts that may be embodied in a wide variety of contexts. The specific aspects and embodiments discussed herein are merely illustrative of ways to make and use the invention, and do not limit the scope of the invention.

In the description which follows like parts may be marked throughout the specification and drawing with the same reference numerals, respectively. The drawing figures are not necessarily to scale and certain features may be shown exaggerated in scale or in somewhat generalized or schematic form in the interest of clarity and conciseness.

Compounds that act to prevent or inhibit uncontrolled cell growth rarely include transition metals. Forms of a compound (and all derivatives and stereoisomers thereof) having at least one transition metal—a ruthenium atom—that has one or more properties similar to platinum are further described herein. Such compounds, in which the ruthenium atom is attached to a redox active ligand and has an overall charge of 2+ or greater, are capable of modifying biologic targets, including DNA, cellular enzymes, cells undergoing uncontrolled growth, and subjects in need thereof, such as those having such biologic targets. Moreover, such compounds exhibit enhanced modifying activity under hypoxic conditions.

In general, compounds as described herein are complexes with at least one ruthenium atom attached to a redox active ligand that may be isolated as a chloride salt. Accordingly, these complexes are stable in water. The compounds are soluble in water as the chloride salts or in acetonitrile as the hexafluorophosphate ($PF_6^-$) salts. The complexes may be monomers, dimers or multimers having at least one ruthenium (Ru) atom attached to a redox active ligand, the complex having an overall charge of 2+ or more.

Such compounds, however, do not typically provide modifying activity unless first reduced with a reducing agent; the reducing agent acting on the redox active ligand. One or more reductions provide for more than one active, reduced species as further described below. Suitable reducing agents include glutathione (GSH), hydrazine, dithiothreitol, ascorbic acid, sodium ascorbate, and sodium borohydride, as examples. Because several suitable reducing agents are typically present in biologic environments, no additional agent need be provided for suitable compounds and compositions to modify a biologic target.

Examples of generic forms of a compound are depicted in Scheme 1A and Scheme 1B. Scheme 1A is a monomeric form comprising a ruthenium atom with an overall charge of 2+ or greater attached to a redox active ligand. Scheme 1B is a dimeric form of the compound comprising two ruthenium atoms, each ruthenium atom bridged or extended by a redox active ligand to maintain separation of the two ruthenium atoms, the dimeric compound having an overall charge of 2+ or more. Additional multimeric forms may also be formed.

Scheme 1A.

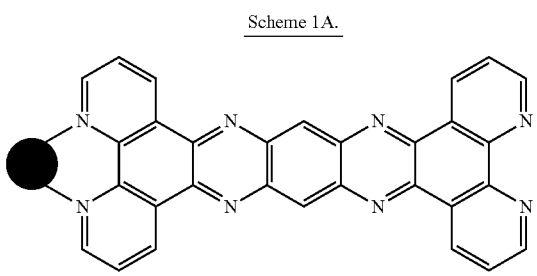

Scheme 1B.

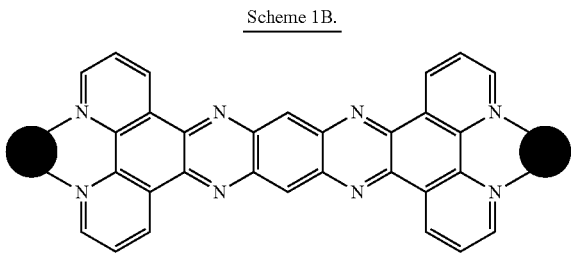

Scheme 2 is another form of a dimeric compound showing the possible substitution sites for the compound. Suitable derivatives involve changing some or all of the R groups (depicted as $R_1$ through $R_{14}$ shown in Scheme 2). Substituents for $R_1$ through $R_{14}$ include, but are not limited to, hydrogen, Group IV elements or halogens, such as fluorine, chlorine, bromine, iodine, as well as oxygen-containing R groups, such as OR', where R' is hydrogen, alkyl or aryl group. In addition, $R_1$ through $R_{14}$ substituents may include nitrogen-containing groups, such as $NH_2$, NR'H, $NR'_2$ (where R' is hydrogen, alkyl or aryl group) or simply aryl or alkyl groups. Various combinations of such substituents may also be used.

Scheme 2.

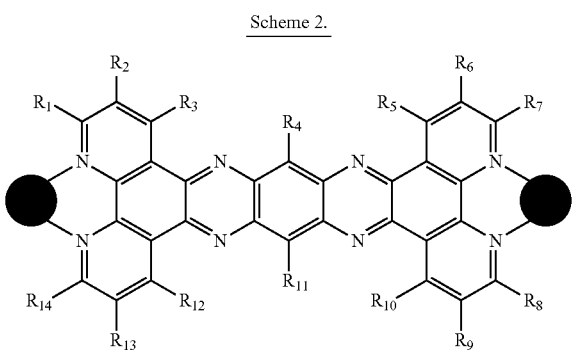

An alternative of Scheme 2 is depicted in Scheme 3 in which $R_4$ and $R_{11}$ comprise oxygen groups; the remaining R groups may comprise any of the substituents as described for Scheme 2.

Scheme 3.

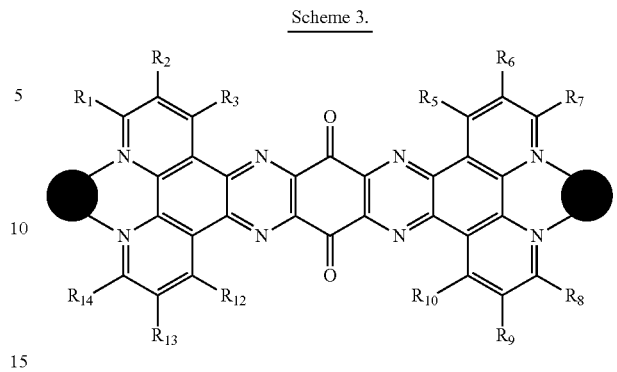

Typical forms often include the at least one ruthenium atom possessing one or more terminal ligands. The one or more terminal ligands form a complex with the ruthenium atom. With two or more complexes, the complexes are extended or bridged by the redox active ligand. However, each complex need not be identical. Accordingly, each ruthenium atom may be complexed to one or more equivalent or differing terminal ligands.

In one form of a compound, a first ligand is complexed with a ruthenium atom, the first ligand generally being a heterocyclic aromatic compound, a planar heterocyclic aromatic compound, a chelating compound or the like. Examples include pyridine, pyrimidine, ethylenediamine, 1,10-phenanthroline, 1,10-phenanthroline-5,6,-dione, 2,2'-bipyridine, phendione, and their derivatives. This complex is attached to a second ligand. The second ligand is redox active and capable of binding to a nucleic acid. The second ligand may also serve as an extension or bridge for two or more ruthenium complexes to maintain separation of the two or more ruthenium complexes. Examples of second ligands include 9,11,20,22-tetraazatetrapyrido[3,2-a:2',3'-c:3",2"-l:2''',3'''-n]-pentacene (also referred to as tatpp), tatpq (9,11,20,22-tetraazatetrapyrido[3,2-a:2',3'-c:3",2"-1:2''',3'''-n]-pentacene-10,21-quinone), tpphz (tetrapyrido[3,2-a:2',3'-c:3",2"-h:2''',3'''-j]phenazine), tppa, dpphz (dipyrido[3,2-a:2',3'-c]phenazine) and their derivatives, as well as any suitable R-group substitutions (as shown in Scheme 2 and Scheme 3) to one or more carbon atoms of the second ligand. The second ligand is often a somewhat rigid molecule (e.g., tatpp or tatpq). When two or more ruthenium complexes are provided, the second ligand maintains separation of Ru—Ru complexes at an appropriate distance, typically between about 12 to 17 Angstroms. More flexible second ligands are also suitable. Ligands, such as tpphz, that are not redox active at biologic potentials, are also suitable.

Suitable dimeric compounds comprise two ruthenium complexes, each complex having a ruthenium atom possessing at least one first ligand and separated by a second ligand. An example is shown in Scheme 4 in which tatpp is the second (bridging or extending) ligand and each complex possesses the same first ligand, which, in this example, is 1,10-phenanthroline (phen). The compound of Scheme 4 is also referred to herein as $[Ru_2(phen)_4tatpp]^{4+}$, $[(phen)_2Ru(tatpp)Ru(phen)_2]^{4}$ or $P^{4+}$. The charged state of the compound is depicted to its right.

Scheme 4.

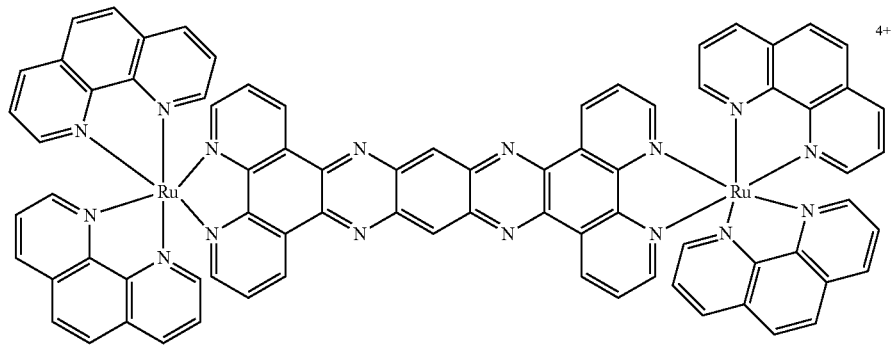

A charged species with an overall charge greater than 2+ is able to undergo one or more reductions to yield a number of active species. For example, reduction of $P^{4+}$ by a reducing agent provides a species depicted in Scheme 5, also referred to herein as $P^{3+}$. The charged state of this compound is depicted to its right.

Scheme 5.

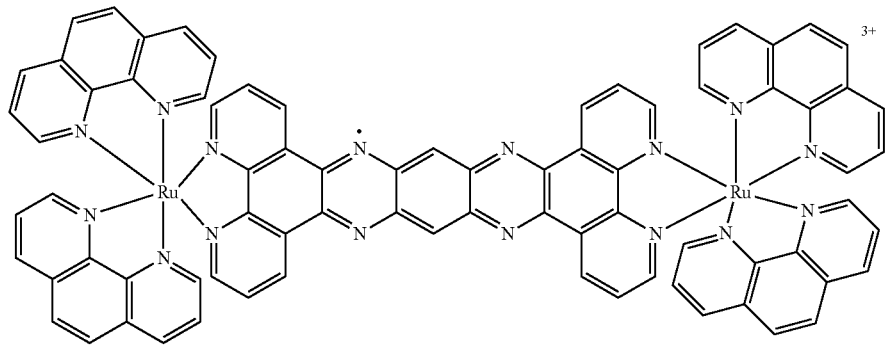

Reactive species, such as the one depicted in Scheme 5, may undergo still further reduction to provide yet another active species. For example, $P^{3+}$ may be thither reduced in the presence of a reducing agent to yield yet another reactive species depicted in Scheme 6 and referred to herein as $[H_2P^{4+}]$. This active species is identified by the doubly reduced, doubly protonated complex. The charged state of this compound is depicted to its right.

Scheme 6.

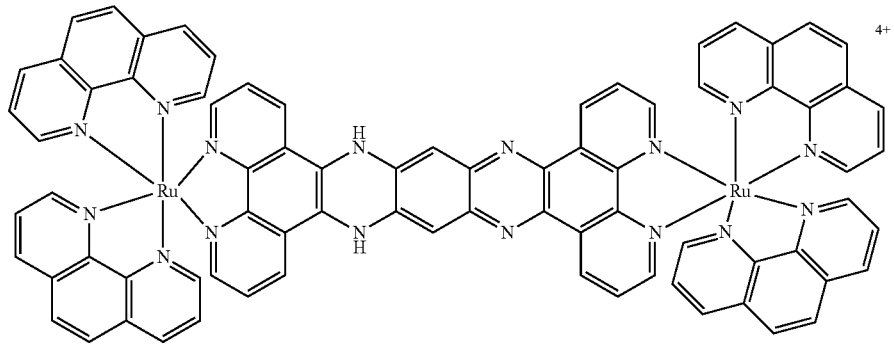

A reduced complex, such as that depicted in Scheme 6, is a suitable compound exhibiting paramagnetic properties. When such a compound comprises an appropriate extending ligand, such as tatpp, the compound may provide a low lying triplet excited state that is partially populated at ambient temperatures. Accordingly, the resulting activity of such a protonated complex may be regenerative due to this diradical state, which is relatively stable. Thus compounds are reductively regenerative (e.g., catalytic) compositions.

Using synthetic methods, such as those described herein, compounds and composition described herein typically includes a number of derivatives and stereoisomers, A monomeric form typically has one to six isomeric forms of its cationic complex, while a multimer will have different enantiomeric forms of its cationic complexes (each cationic complex comprising an Ru atom possessing at least one terminal ligand). For a dimeric compound with two cationic complexes each acting as a chiral center, there are 12 compound derivatives. An example is $P^{4+}$, a dimer containing a tatpp bridge.

Figure 2:
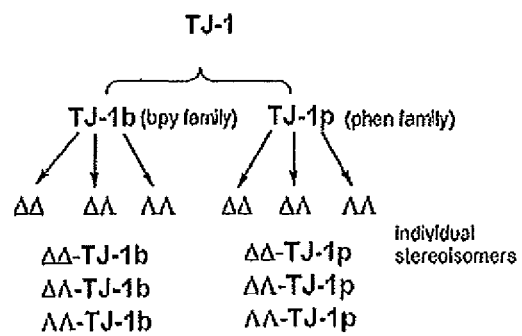
FIG. 2 depicts a schematic of stereoisomer combinations possible for two suitable compositions.

General synthesis of suitable compounds may rely on methods known to one of ordinary skill in the art (See, for example, Kim et al., Inorg. Chem. 2002:41;2471-2476). In addition, a series of cationic Ru (II) polypyridyl dimeric compounds are synthesized by methods provided by one of the inventors, Frederick MacDonnell, for the construction of enantiopure complexes containing multiple chiral centers. These methods include stereospecific synthetic routes using one of the reactions as outlined in FIG. 1, where the Δ and Λ signify the absolute stereochemistry at each Ru(II) center. In FIG. 1, each complex is prepared with at least one terminal ligand of bipyridine (b or bpy) or phenanthroline (p or phen). Referring now to FIG. 2, each b derivative is resolvable into the enantiomers, such as ΔΔ-TJ-1b and ΛΛ-TJ-1b, and the meso complex, such as ΔΛ-TJ-1b. Similarly the p derivatives are resolved. In this manner, numerous complexes are possible, with each TJ complex generally having a total of six isomers (unless there is only one chiral center and therefore fewer stereoisomers). A dimeric compound containing the same bridging ligand typically has 12 compound derivatives, assuming a chiral center for each ruthenium complex.

As shown in FIG. 1, ΔΔ compositions and their optical antipodes ΛΛ as well as the diastereomeric, mesa complex ΔΛ are formed by choosing the appropriate enantiopure monomers (which are resolved). Typically, the ΔΛ-isomer is equivalent to the ΛΔ-isomer and is not chiral due to an internal mirror plane symmetry element. In this manner, stereoisomers in enantiopure form may be prepared when necessary. When stereochemical purity is not important, compositions comprise a diastereomeric mixture of the ΛΛ, ΔΔ and ΔΛ isomers.

Figure 3:
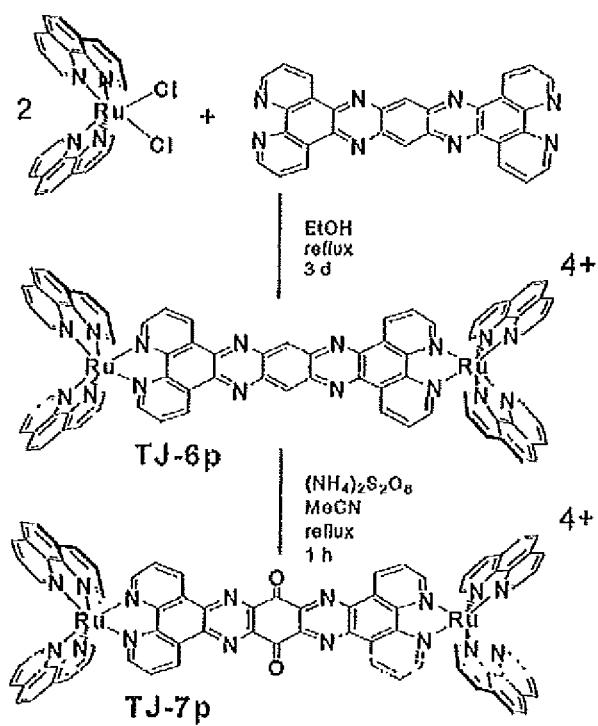
FIG. 3 depicts a schematic of a high yield but non-stereospecific route for preparation of a one or more suitable compositions.

A convenient, high yield but non-stereospecific route to forming one or more compositions may also used as outlined in FIG. 3. Using TJ-6p and TJ-7p as examples, the procedure for TJ-6p involves displacement of chloride ligands on [Ru(phen)$_2$Cl$_2$] with a tatpp ligand. The quinone TJ-7p is readily prepared via ammonium persulfate oxidation of TJ-6p in nearly quantitative yield.

Multimeric compounds generally fall into families that depend on the choice of the bridging or extending ligand. As examples, a first family comprises compounds having Ru atom complexes with shorter (~12 Å long) bridging ligands (e.g., tpphz), while a second family comprises compounds with longer (~17 Å) bridging ligands (e.g., tatpp, tatpq). Additional families are formed by bridging ligands of other lengths.

Figure 4:
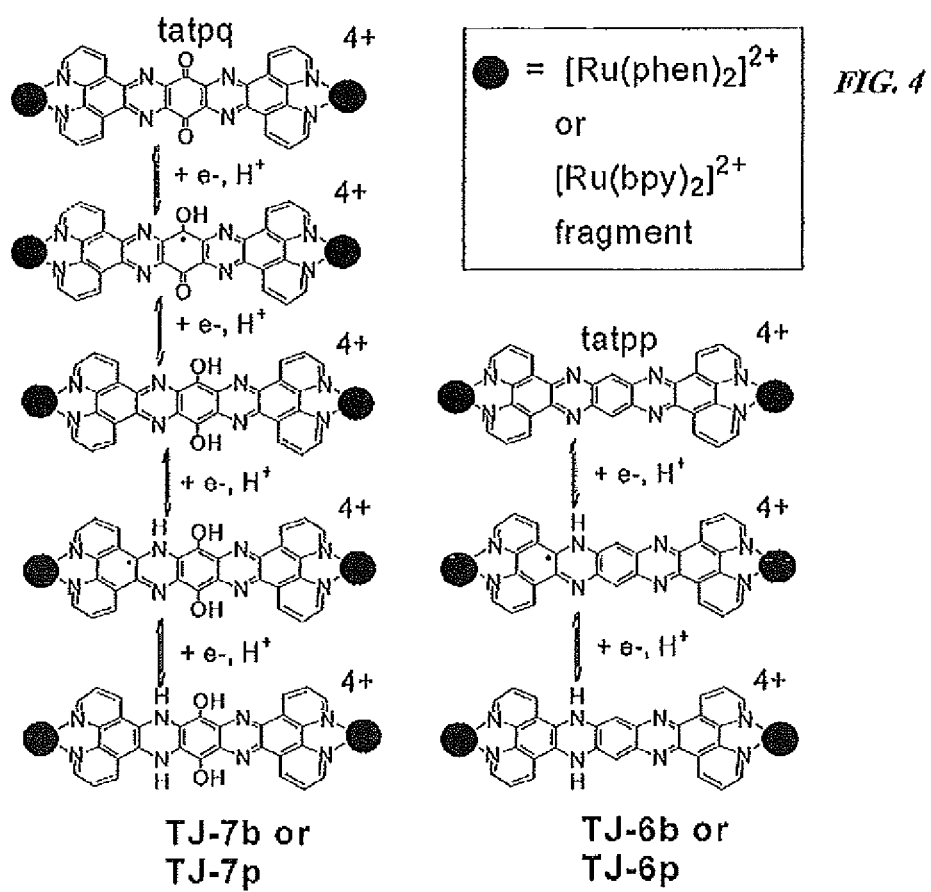
FIG. 4 depicts multiple, reversible redox and protonation states for suitable redox active ligands.

Bridging or extending ligands typically exhibit multiple, reversible redox states. This is depicted in FIG. 4 in which compounds having a tatpp or tatpq bridging ligand are provided as examples. Preferred bridging ligands have modest potentials in order for them to be accessible in a cellular milieu. For example, cyclic voltammetry in aqueous solution with TJ-6p of FIG. 2 (having tatpp as a bridging ligand) showed that the first two reductions for this compound occurred at 170 mV and −180 mV. For TJ-7p of FIG. 2, a compound in which tatpq is the bridging ligand, the first two reductions were at 70 mV and −80 mV versus the normal hydrogen electrode. These potentials are modest and easily accessible in a cellular milieu.

Suitable compounds are generally capable of forming a tight interaction with DNA. While this ability is similarly known for other metallointercalators, none of the known metallointercalators modify cells (e.g., damage DNA) under hypoxic conditions and in the absence of an additional agent, such as via photoexcitation, Other known compounds also function differently than those described herein by activation of dioxygen to generate reactive oxygen species (ROS), such as hydroxyl radicals and superoxide radicals. And it is these ROS that are ultimately responsible for the DNA damage by other known metallointercalators. In addition, unlike compounds described herein, other metallointercalators are insensitive to the oxygen environment (pO$_2$) and thus do not specifically target hypoxic cells (e.g., tumor cells).

Such compounds intercalate with and/or bind to DNA. Typical binding constants ($K_b$) for most suitable compounds are about $10^6$ to $10^{10}$ M$^{-1}$. Those containing a single Ru center (2+ overall charge) have binding constants on the order of $10^7$ M$^{-1}$ whereas ones containing two Ru atom centers (4+ overall charge) have binding constants as high as $10^{10}$ M$^{+1}$. Using $P^{4+}$, as an example, its $K_b$ value is about $K_b \sim 10^{10}$ M$^{+1}$ in a standard assay using buffered Tris-salt solutions (e.g., 10 mM Trischloride, pH 7.5 with 10 mM NaCl or 50 mM NaCl).

Figure 5:
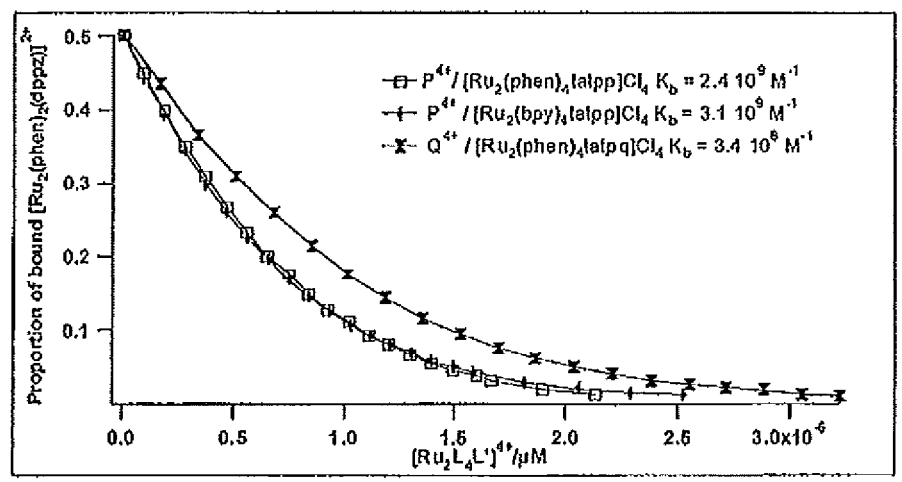
FIG. 5 depicts DNA binding curves for several representative compositions.

Binding to DNA by suitable compounds are likely to cause cellular apoptosis, because nuclear DNA appears to be the primary cell target for these compounds, DNA binding of various compounds are illustrated in FIG. 5, showing such compounds bind DNA tightly with an equilibrium binding constant ($K_b$) of at least about $10^8$ to $10^{10}$ M$^{-1}$. For FIG. 5, an in vitro analysis was performed using an intercalator displacement titration with calf-thymus DNA in a buffer (10 mM Tris, 10 mM NaCl, pH 7.5). The intercalator was a ruthenium complex Δ-[Ru(phen)$_2$(dppz)]$^{2+}$ known to have a Kb of 5×10$^7$M$^{-1}$, binding site size of 2 and only fluoresces when intercalated into the DNA. None of the other compounds used except Δ-[Ru(phen)$_2$(dppz)]$^{2+}$ fluorescence in the presence or absence of DNA. Binding constants were determined by making a solution of 10 μM Δ-[Ru(phen)$_2$(dppz)]$^{2+}$ and 4 μM calf-thymus DNA and monitoring sample fluorescence as another compound was titrated in. In FIG. 5, phen refers to the terminal ligand: 1,10-phenanthroline; bpy is the terminal ligand: 2,2'-bipyridine; and tatpq is the bridging ligand: [Ru$_2$(phen)$_4$tatpp]Cl$_4$, [Ru$_2$(bpy)$_4$tatpp]Cl$_4$) is one active form of $P^{4+}$. $Q^{4+}$ is one active form also referred to herein as ([Ru$_2$(phen)$_4$tatpq]Cl$_4$).

Fitting the data from FIG. 5 to the McGhee-von Hippie equation as known to one of ordinary skill in the art yielded binding constants ($K_b$) and binding site size (s) shown in the TABLE. Binding constants ranged from $10^7$ to $10^{10}$ M$^{-1}$ showing extremely tight binding to double stranded DNA. The TABLE also depicts relevant IC$_{50}$ and LD$_{50}$ determined for such compounds. The absorption spectra for each of these compounds (not shown) also showed a 20-40% hypochroism and 4-6 nm red shift of the band associated with an electronic transition on the bridging ligand which supports the intercalative mode of binding for each compound. For the TABLE, n.d.= not determined, (a) is the maximum dose due to poor solubility and (b) are compounds identified us acutely toxic with a single animal, tested at 0.2 mg in 200 μL buffer (about 6.0 mg/kg).

TABLE

DNA binding constants, $IC_{50}$ and $LD_{50}$ data.

| Compound | Kb (s) | $IC_{50}$ (μM) | MTD (mg/kg) |
|---|---|---|---|
| $[Ru_2(bpy)_2(tpphz)(C_2O_4)_2]$ | n.d. | 100 ± 10 | >15[a] |
| $[Ru_2(bpy)_2(tpphz)(CO)_4]^{4+}$ | $2.6 \times 10^7$ (1.3) | 12 ± 1 | >6[a] |
| $[Ru_2(bpy)_2(tpphz)(CH_3CN)_4]^{4+}$ | $9.4 \times 10^9$ (2.5) | 21 ± 2 | <6[b] |
| $[Ru_2(bpy)_2(tpphz)(CO)_2(Cl)_2]^{4+}$ | n.d. | 8 ± 1 | <6[b] |
| $[Ru_2(phen)4(tatpp)]^{4+}$ | $2.4 \times 10^9$ (2.2) | 8 ± 1 | 67 |
| $[Ru_2(phen)4(tatpq)]^{4+}$ | $3.4 \times 10^8$ (1.7) | 1 ± 0.1 | 17 |

The reduction potential for compounds is such that these compounds are accessible to one or more reducing agents, especially in biologic conditions. For example, the bridging ligand, tatpp, when bound by two ruthenium ions in $P^{4+}$, has a reduction potential ($B_{1/2}$) of about −0.22 V versus Ag/AgCl in acetonitrile. An alternate charged form of $P^{4+}$, $P^{3+}$, has an $E_{1/2}$ of about −0.71 V versus Ag/AgCl in acetonitrile. These $E_{1/2}$ values of the complexes make them accessible to one or more suitable reducing agents in biologic conditions.

Cell and Animal Modification Examples.

Under hypoxic conditions and in the presence of a reducing agent, compounds described herein are capable of modifying supercoiled DNA (i.e., Form 1). Modification includes breaking or cleaving at least one or both strands of the DNA. For example, the $P^{4+}$ complex breaks DNA to provide either a circular form (i.e., Form II) with a single strand break or a linear form (Form III) upon breaking both stands in close proximity. These modifications typically occur in the presence of a very low concentration of the compound. At varying concentrations of $P^{4+}$, the efficiency of DNA strand breaks remained at about one $P^{4+}$ for every 12 base pairs of a DNA, Further examples are provided herein.

Figure 6:
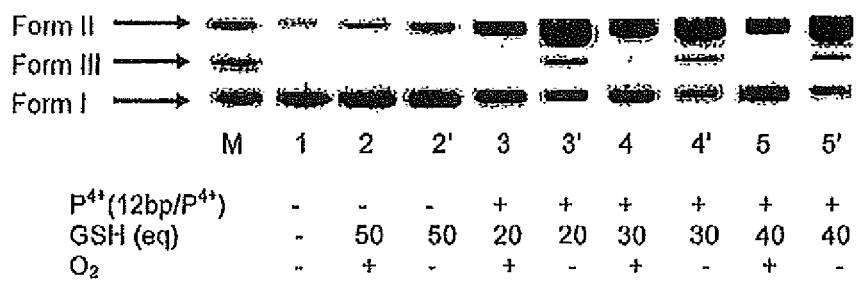
FIG. 6 depicts DNA modifying activity of a representative composition in the presence of varying concentrations of a reducing agent in the presence and absence of oxygen.

Referring now to FIG. 6, supercoiled DNA (0.154 mM base pairs) was modified by a diastereomeric mixture of the $P^{4+}$ complex in the presence and absence of a reducing agent. Lane M was the marker lane. Lane 1 was a DNA control without a reducing agent. Lane 2 included DNA without $P^{4+}$ under aerobic conditions (e.g., in the presence of oxygen or $O_2$) with GSH, Lane 2' included DNA with GSH (0.513 mM) without $P^{4+}$ under anaerobic conditions (e.g., hypoxia). Lanes 3, 4 and 5 were representative of modifications under aerobic ($O_2$) conditions and lanes 2', 3', 4' and 5' were representative of modifications under anaerobic (hypoxia or absent $O_2$) conditions. Lane 3 and 3' included DNA with $P^{4+}$ (0.0128 mM) and GSH (0.256 mM); lane 4 and 4' included DNA with $P^{4+}$ (0.0128 mM) and GSH (0.384 mM); and lane 5 and 5' included DNA with $P^{4+}$ (0.0128 mM) and GSH (0.512 mM).

FIG. 6 shows that $P^{4+}$ modified or converted supercoiled DNA (Form I) to circular DNA (Form II) by a single strand scission. With removal of dissolved oxygen from the reaction there was a substantial increase in activity of $P^{4+}$ represented by an increase in the amount of DNA modified or broken by the $P^{4+}$ complex, including both circular DNA via single strand breaks and linear DNA (Form III) caused by double strand nicks. Adjustments in the reducing agent concentration did not effect the efficiency of $P^{4+}$ to modify or break DNA strands, but remained at about one $P^{4+}$ for every 12 base pairs of a DNA. FIG. 6 demonstrates the ability to modify DNA independent of oxygen (oxygen-independent modification) when a reducing agent was present. Under such conditions, a representative compound displayed improved activity under anaerobic conditions (single stranded breaks were potentiated and most of the supercoiled DNA was transformed).

Modification reactions were carried out in 0.5 mL Eppendorf tubes with 2 μL of a supercoiled pUC18 DNA (1 μg/1 μL) in a total volume of 20 μL using a 5 mM sodium phosphate buffer (pH 7). GSH, as the reducing agent, was generally used at concentrations of at least one $P^{4+}$ for every 12 base pairs. All reactions were allowed to equilibrate for about 1 hour at ambient temperatures (e.g., 25 degrees Centigrade). After equilibration, DNA was precipitated (e.g., adding 2 μL, sodium acetate at pH 5.2 and 80 μL ethanol followed by cooling overnight at −20 degrees Centigrade). DNA was then dried for about 30 minutes and resuspended in about 40 μL of a storage buffer (e.g., 40 mM Tris-Cl, 1 mM EDTA at pH 8.0) with 65 μL of deionized water and 12 μL of a loading buffer (e.g., 30% glycerol in water with 0.1% w/v bromophenol blue), Each reaction was then evaluated by standard gel electrophoresis methods (e.g., loaded on 1% agarose gel stained with ethidium bromide and electrophoresed at about 80 volts for about 90 minutes using a Tris-acetate-EDTA buffer at pH 8.0).

Modifications under anaerobic conditions included degassing all the reagents (including the DNA) before equilibration by subjecting each to about four freeze-pump-thaw cycles under nitrogen gas. Such samples were typically stored and handled inside a glove box to minimize further contamination with oxygen.

Figure 7:
FIG. 7 depicts DNA modifying activity of a representative composition in the presence and absence of oxygen.

FIG. 7 is a further example depicting an ability of representative compounds to modify DNA in the presence and absence of oxygen, and particularly, its ability to modify DNA independent of oxygen when reduced. Here, activity in the presence and absence of oxygen were compared for the $P^{4+}$ complex at 12.8 μM (see lanes 3', 4, 4'), the oxygen-dependent Iron(II)-Bleomycin (Fe-BLM) at 12.8 μM (see Lane 5 and 5') in the presence and absence of a reducing agent (GSH at 0.153 mM; see lanes 2', 4, 4'). Fe-BLM was used because activity of this agent is considered oxygen dependent; it can induce single strand DNA breaks but not double strand DNA cuts under anaerobic conditions.

FIG. 7 showed that compounds were capable of providing both single strand and double strand breaks of DNA. There was improved activity when such compounds were reduced and in an oxygen-free environment (lane 4'). This was in contrast to Fe-BLM which was unable to modify or break DNA in the absence of oxygen (lane 5'). Overall, compounds are even more effective at modifying DNA under reduced and hypoxic conditions (e.g., DNA single strand breaks were potentiated and most of the supercoiled DNA was transformed).

Modification reactions for FIG. 7 were performed with conditions similar to those described for FIG. 6, in which supercoiled pUC18 DNA (0.154 mM base pairs) was used with different modifying agents, namely Fe-ELM and the $P^{4+}$ complex, Incubation times were about one hour. For FIG. 7, lane M was the marker. Lane 1 was a DNA control. Lane 2' included DNA with GSH. Lane 3' was DNA with the $P^{4+}$ complex under anaerobic (hypoxic) conditions. Lane 4 was DNA with $P^{4+}$ complex and a reducing agent under aerobic conditions. Lane 4' was lane 4 under anaerobic conditions. Lane 5 was DNA with Fe-BLM under aerobic conditions. Lane 5' was lane 5 under anaerobic conditions. Quenching of activity of $P^{4+}$ and Fe-BLM was performed under anaerobic conditions by precipitating the DNA using about 2 μL of degassed sodium acetate (pH 5.2) and 80 μL of degassed ethanol under nitrogen gas.

Figure 8:
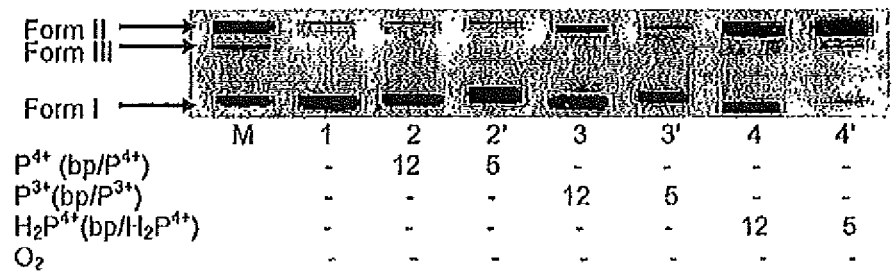
FIG. 8 depicts DNA modifying activity of several representative compositions in a hypoxic environment.

Modifying activity as shown herein is not typically dependent on radical species of the reducing agent, such as a glutathyl radical when GSH is used as the reducing agent, as shown in FIG. 8. Here, reduced forms of $P^{4+}$ were prepared and purified to provide pure $P^{3+}$ [(phen$_2$Ru(tatpp$^{...}$)Ru(phen)$_2$] and pure [H$_2$P$^{4+}$] [(phen)$_2$Ru(H$_2$tatpp)Ru(phen)$_2$]. As shown in FIG. 8, all reduced forms (e.g., $P^{3+}$ and [H$_2$P$^{4+}$]) modified supercoiled DNA in a hypoxic environment by breaking one strand and/or both strands of DNA. For FIG. 8, supercoiled pUC18 DNA (0.154 mM base pairs) was modified by $P^{4+}$, $P^{3+}$ and [H$_2$P$^{4+}$] under nitrogen gas as described for FIG. 7, and otherwise as described for FIG. 6 (except that each reaction was equilibrated for about three hours in the absence of the reducing agent and under hypoxic conditions). For FIG. 8, Lane M was the marker. Lane 1 was a DNA control. Lane 2 was DNA with $P^{4+}$ (12.8 μM). Lane 2' was DNA with $P^{4+}$ (31.0 μM). Lane 3 is DNA with $P^{3+}$ (12.8 μM). Lane 3' was DNA with $P^{3+}$ (31.0 μM). Lane 4 was DNA with [H$_2$P$^{4+}$] (12.8 μM). Lane 4' was DNA+[H$_2$P$^{4+}$] at 31.0 μM.

FIG. 8 also revealed that the doubly reduced form or [H$_2$P$^{4+}$] modified DNA to provide both single strand breaks and double strand breaks (lanes 6 and 7). $P^{3+}$ showed an ability to nick single stranded DNA (lanes 4 and 5). Because [H$_2$P$^{4+}$] consistently promoted both single and double strand breaks and $P^{4+}$, alone, does not, this may be used to suggest $P^{4+}$ is a prodrug capable of being converted to the most active form, [H$_2$P$^{4+}$], in situ via reduction. This is further evidenced by noting that when $P^{4+}$ and excess GSH were incubated in the appropriate buffer under anaerobic conditions, the visible portion of the absorption spectrum matched that for [H$_2$P$^{4+}$] in water at pH 7 (see FIG. 10). In addition, because higher concentrations of [H$_2$P$^{4+}$] and longer reaction times were required to see linear DNA in the absence of a reducing agent (see FIG. 8, lane 4') as compared to when a reducing agent was present in situ (as in FIG. 7), [H$_2$P$^{4+}$] may be catalytic in its activity.

Figure 11:
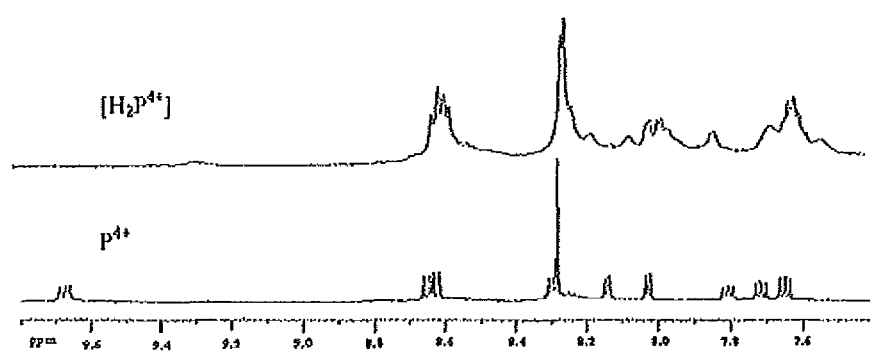
FIG. 11 depicts $^1H$ NMR spectra of suitable compositions.
Figure 12:
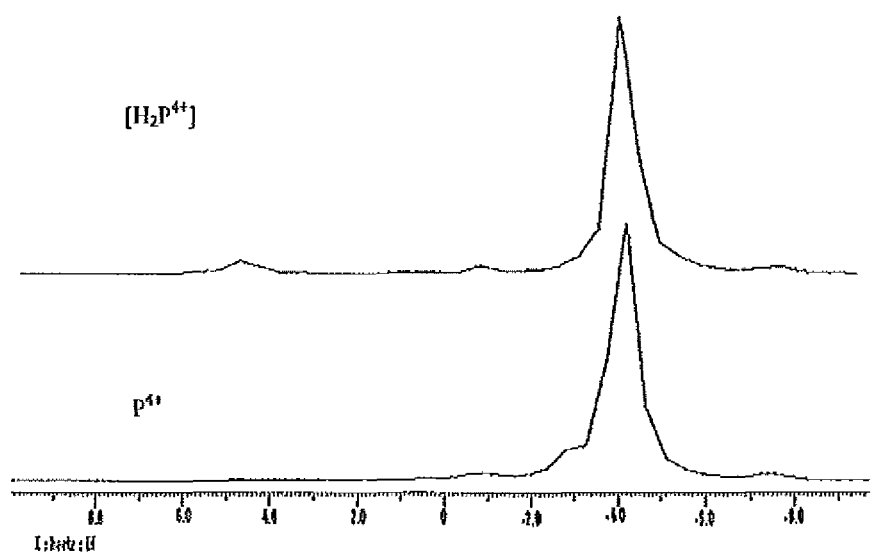
FIG. 12 depicts Evans's method NMR measurement of $\mu_{eff}$ for representative compositions.

This is supported by the fact that H$_2$P$^{4+}$ exhibits paramagnetic properties as determined by $^1$H-NMR and Evans method paramagnetic susceptibility measurements (FIG. 11 and FIG. 12, respectively). The broadness of the peaks in the top spectra of FIG. 11 is typical of a paramagnetic species. Both spectra in FIG. 11 were overlaid $^1$H NMR (500 MHz, CD$_3$CN) spectra for hexafluorophosphate salts of $P^{4+}$ [(phen)$_2$Ru(tatpp$^{...}$)Ru(phen)$_2$][Cl]$_3$ ([P]Cl$_3$) and H$_2$P$^{4+}$ [(phen)$_2$Ru(H$_2$tatpp)Ru(phen)$_2$][Cl]$_4$([H$_2$P]Cl$_4$)] at 25 degrees Centigrade. FIG. 12 shows Evans method magnetic susceptibility determination for [H$_2$P$^{4+}$] (top spectra) and $P^{4+}$ (bottom spectra) using the same experiment; $P^{4+}$ being used as a diamagnetic control. This method gives a $\mu_B$ of 1.0 BM for [H$_2$P$^{4+}$] in deuterated acetonitrile solution. For FIG. 12, the mass of the [H$_2$P$^{4+}$] was 15 mg, which was dissolved in 0.8 mL of deuterated CD$_3$CN containing 4% TMS. The weight of 0.8 mL CD$_3$CN in TMS solution was 0.645 g; Δf=[(4.44−(−4.27)]; Hz=8.71 Hz; f=500 MHz; $\chi_{para}$=0.422×10$^{-3}$ emu/mol; and $\mu_{eff}$=2.828 (0:422×10$^{-3}$* 298)$^{1/2}$1.00 B.M.

Accordingly, the reduced form, which, in this case is [H$_2$P$^{4+}$], appears to have catalytic activity and paramagnetism. The paramagnetism is due to a low lying triplet excited state on the bridging or extending ligand that is partially populated at ambient temperatures. The resulting activity of the doubly reduced form, [H$_2$P$^{4+}$], appears to be due to this diradical state.

Figure 9:
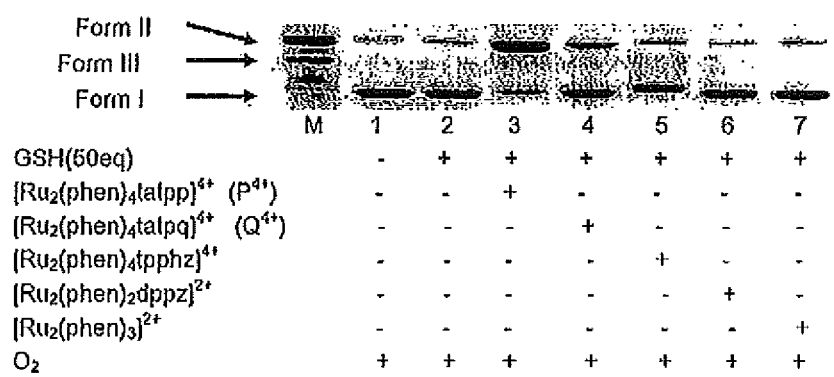
FIG. 9 depicts DNA modifying activity of several representative compositions in the presence of a reducing agent.

FIG. 9 depicts the DNA modifying activity of a number of suitable compounds. For each compound, a first ligand possessed by each Ru(II) complex was phen (1,10-phenanthroline), whereas differing second ligands as extending or bridging ligands were used, namely, tatpp, tatpq, tpphz, or dppz. Schematics of these compounds are depicted in FIGS. 13A to 13E.

Reaction conditions for FIG. 9 were as described for FIG. 6 and FIG. 7, in which supercoiled pUC18 DNA (0.154 mM base pairs) was used with one of the compounds at a concentration of 0.0128 mM in the presence of a reducing agent (GSH at 0.641 mM) in an oxygen environment, Only lane 1 had no reducing agent. Lane M was the marker. Lane 2 was DNA alone, which was compared to compounds, including $P^{4+}$ (lane 3), [Ru$_2$(phen)$_4$tatpq]$^{4+}$ (lane 4), [Ru$_2$(phen)$_4$tpphz]$^{4+}$ (lane 5), [Ru(phen)$_2$dppz]$^{2+}$ (lane 6), and [Ru(phen)$_3$]$^{2+}$ (lane 7).

Suitable compounds typically exhibit DNA modifying nativity under a wide range of pH conditions. As shown in FIG. 18, a diastereomeric mixture of $P^{4+}$ is active at pH 6.0 to pH 11, in the presence and absence of a reducing agent. Here, reaction conditions resemble those described for FIG. 6 except that the reaction was incubated for at least about 2 hours under nitrogen gas. FIG. 18 indicates the reduced and active species of $P^{4+}$, including [H$_2$P$^{4+}$], may have a number of protonation states and still remain active.

Figure 10:
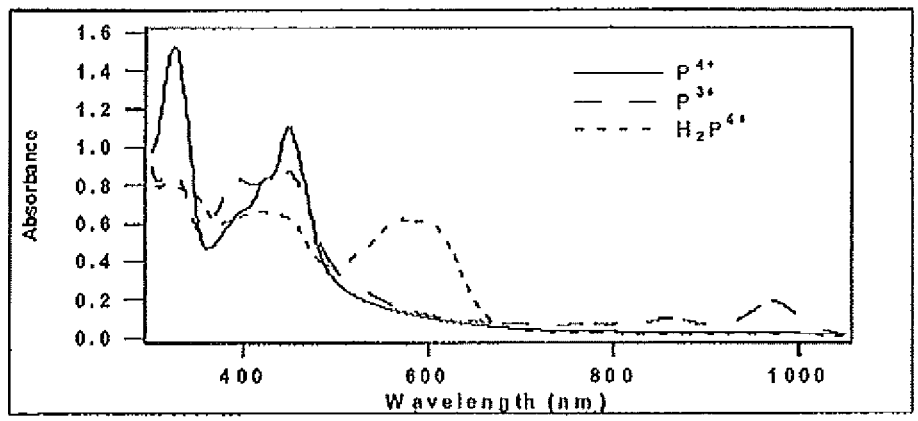
FIG. 10 depicts a representative absorption spectra for several representative compositions.
Figure 13A:
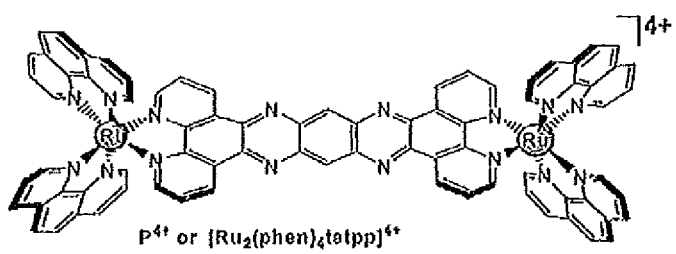
Figure 13B:
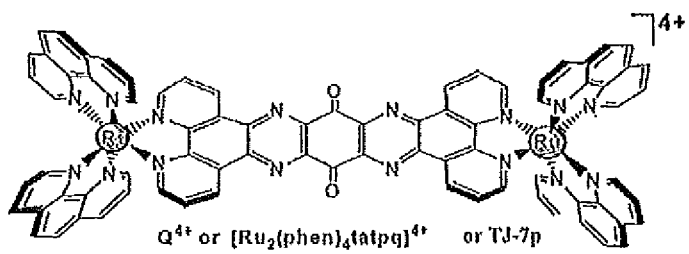
Figure 13C:
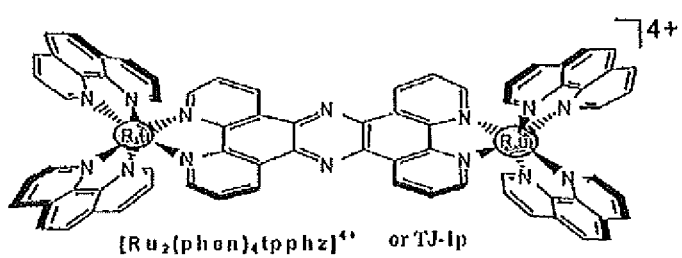
Figure 14A:
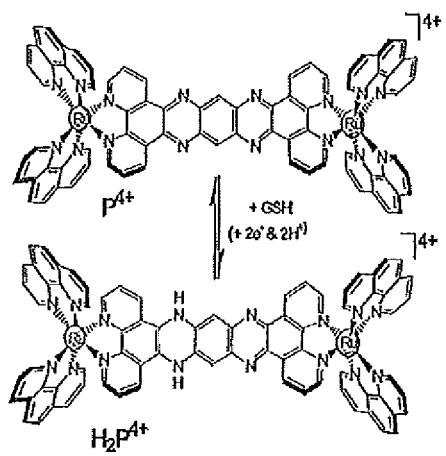
FIGS. 14A and 14B depicts schematics of several representative compositions.
Figure 14B:
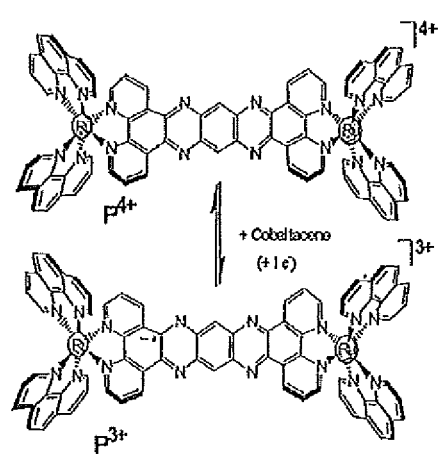

Now referring to FIG. 14A, a schematic of the reduction of $P^{4+}$ to the double protonated form [H$_2$P$^{4+}$] is shown, FIG. 14B shows a schematic of $P^{4+}$ and its chemical conversion to the reduced form, $P^{3+}$, using cobaltacene. In general, syntheses of these compounds were performed under nitrogen atmosphere inside a glove box. $P^{3+}$ was synthesized by reducing $P^{4+}$ with one equivalent of one electron donor (e.g., cobaltacene) in a degassed solution of acetonitrile. After reduction, $P^{3+}$ was further precipitated (e.g., using degassed ether), [H$_2$P$^{4+}$] was synthesized by stirring [P]Cl$_4$ salt in degassed water with 5 equivalent of a reducing agent, such as GSH. Excess GSH was removed by precipitating the formed [H$_2$P$^{4+}$] as hexafluorophosphate salt, which is non soluble in water. Both $P^{3+}$ and [H$_2$P$^{4+}$] structures were confirmed by UV-visible spectroscopy (FIG. 10). The concentration of each species in FIG. 10 is about 26 μM, in which $P^{4+}$ is equivalent to TJ-6p, $P^{3+}$ is the monoreduced form of TJ-6p and [H$_2$P$^{4+}$], the doubly reduced, doubly protonated form of TJ-6p. The absence of any reducing agents in the synthesized forms were confirmed by running $^1$H NMR (see FIG. 11), wherein GSH absence was confirmed for [H$_2$P$^{4+}$] in deuterated water and cobaltacene absence was confirmed for $P^{3+}$ in CD$_3$CN.

Figure 15:
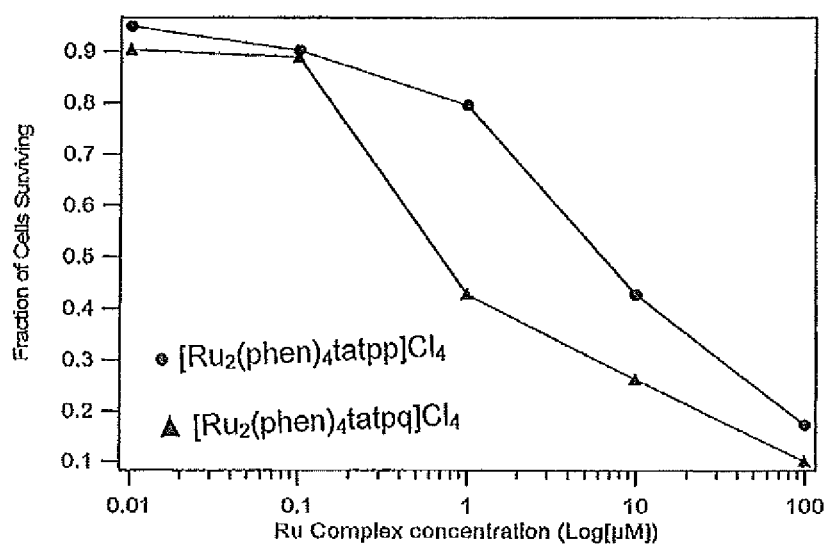
FIG. 15 depicts cell modifying activity for several representative compositions.

Suitable compounds are active in cells and animals. More importantly, these compounds are not cytotoxic to cells, as represented in FIG. 15, in which drug sensitivity assay for such compounds are shown; circles representing data for [Ru$_2$(phen)$_4$tatpp]Cl$_4$ ($P^{4+}$) and triangles representing data for [Ru$_2$(phen)$_4$tatpq]Cl$_4$ ($Q^{4+}$).

For cytotoxicity of suitable compounds a standard MTT drug sensitivity assay was performed on cancer cells, including H358, a bronchioalveolar non-small cell lung cancer cell line. Cell density in an aliquot of cells growing in log phase was determined by counting trypan blue excluding cells in a hemocytometer and 20,000 cells were plated into each well of 96-well flat-bottomed microliter plates. After 24 hours incubation at 37 degrees Centigrade, cell medium containing a compound was added to cells for a final concentration of 0.01, 0.1, 1.0, 10 or 100 µM, After 96 hours of incubation, the $IC_{50}$ of each RPPD was measured by MTT assay (using eight replicate wells for each $IC_{50}$ measurement point, Measured absorbance values were directly linked with a spreadsheet for calculation of $IC_{50}$, which was defined as concentration of compound that reduced formazan formation by 50%. Representative $IC_{50}$ values are presented in the TABLE.

Compounds with respect to their cytotoxicity provides: $[Ru_2(phen)_4(tatpq)]^{4+}$ (1±0.1 µM)>$[Ru_2(phen)_4(tatpp)]^{4+}$ (8±1 µM)~$[Ru_2(bpy)_2(tpphz)(CO)_2(Cl)_2]^{4+}$ (8±1 µM), $[Ru_2(bpy)_2(tpphz)(CO)_4]^{4+}$ (1±0.1 µM), $[Ru_2(bpy)_2(tpphz)(CH_3CN)_4]^{4+}$>(21±2 µM)>$[Ru_2(bpy)_2(tpphz)(C_2O_4)_2]$ (100±10 µM). Compounds with longer bridges appear among the most cytotoxic in cancer cells.

Animal toxicity screens were performed by intraperitoneal injection of suitable compounds in C57BL/6NTac mice (each with an approximate weight of 30 g). For each animal, 0.2 mg of each compound in 200 µL 10 mM Tris buffer, pH 7.5 was used. All of the cationic complexes with tpphz bridges were lethal at this minimal dose (MTD<6 mg/kg), A more neutral dimer with a short tpphz bridge showed poor solubility and was administered up to a maximum dose of 15 mg/kg at which no toxicity was observed. Mice treated with the long tatpp and tatpq bridged complexes survived (e.g., $[Ru_2(phen)_4(tatpp)]^{4+}$, $[Ru2(phen)_4(tatpq)]^{4+}$). These were further examined by injecting at least three mice with 200 µL of a freshly prepared aqueous solution of each compound at concentrations of 0.5 mg/mL, 2 mg/mL, 5 mg/mL, 10 mg/mL, 25 mg/mL and 50 mg/mL to determine MTD values. $[Ru_2(phen)_4(tatpp)]^{4+}$ was found to have a MTD of 67 mg/kg and $[Ru_2(phen)_4(tatpq)]^{4+}$ a MTD of 17 mg/kg.

Accordingly, compounds with longer bridging ligands or those that are more neutral are less acutely toxic to animals. This may be due to their overall size and/or lack of charge, preventing them from forming a close association with the putative target, acetylcholinesterase (AChE), an enzyme responsible for the hydrolysis of acetylcholine. Compounds with short tpphz bridges are acutely toxic, presumably via inhibition of AChE.

Figure 16:
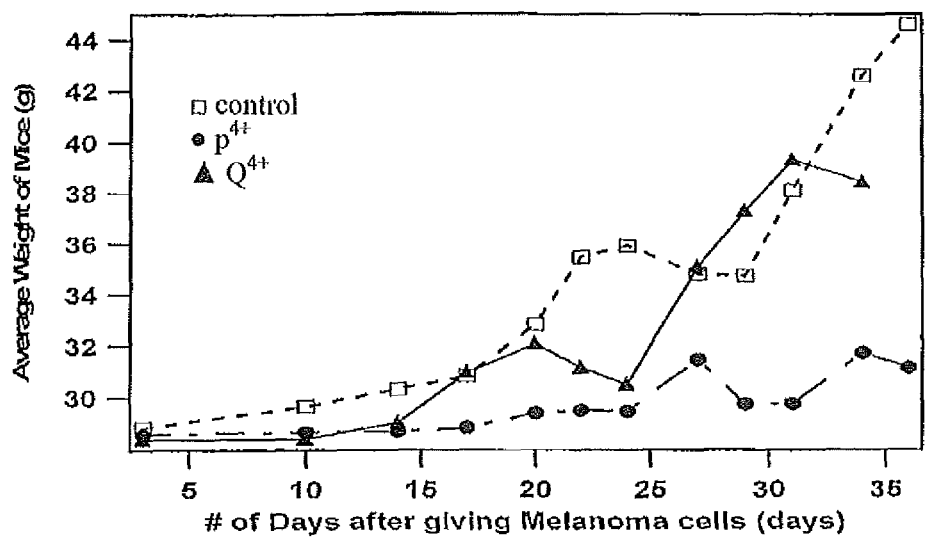
FIG. 16 depicts modifying activity for several representative compositions in animals, wherein squares represent data for control animals, circles for $P^{4+}$ and triangles for $Q^{4+}$.
Figure 17:
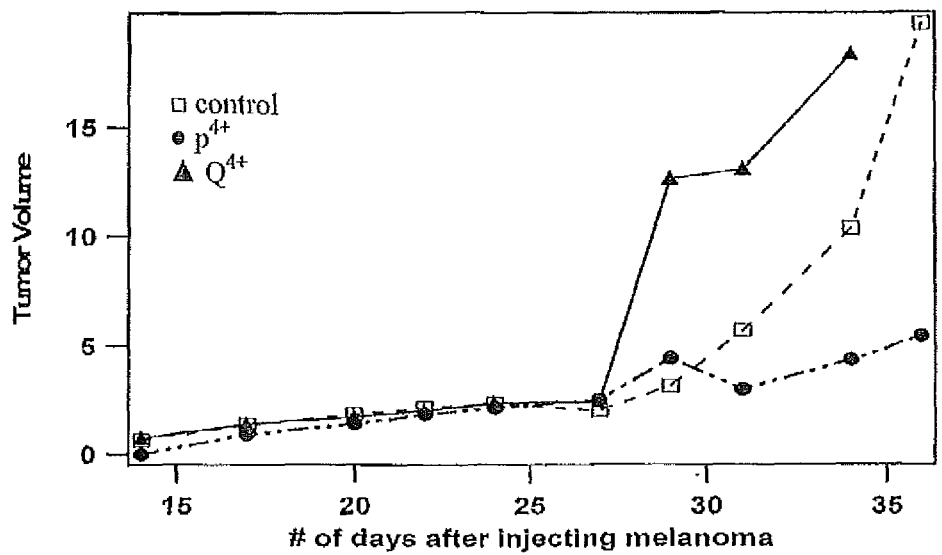
FIG. 17 depicts modifying activity for several representative compositions in animals, wherein squares represent data for control animals, circles for $P^{4+}$ and triangles for $Q^{4+}$.

Suitable compounds also exhibit anti-cancer activity. They are found to suppress tumor growth as demonstrated using an orthotopic syngeneic mouse melanoma model. Mice were subcutaneously injected with approximately one million mouse melanoma cells to initiate tumorigenesis. Animals were grouped and, after four days, each group was injected with a compound combined with a suitable carrier ($P^{4+}$ or $Q^{4+}$) or with carrier alone (as a control). Injections were performed intraperitoneally as 0.2 mg in 100 µL of a buffer and were administered three times a week for two weeks. Changes in animal body weight (FIG. 16) and tumor volume (FIG. 17) were recorded every two to five days for over 35 days. Tumor volume was calculated by measuring the tumor with calipers on the long (b) and short (a) axes using the formula $V=(\pi/6)a^2b$. For FIGS. 16 and 17, squares represent data for control animals, circles for $P^{4+}$ and triangles for $Q^{4+}$. Overall, animal body weight was least affected and tumor growth (as measured by tumor volume) minimized as well as significantly delayed in mice administered $P^{4+}$ as compared to control mice.

Compounds generally modify enzyme activity, particularly enzymes that contribute to cell growth and cell division (e.g., involved in DNA repair/replication) and impulse transmission. For example, compounds were shown to modify activity of topoisomerase I (Topo I) and topoisomerase II (Topo II), enzymes that are abundant in rapidly dividing cells (e.g., tumor cells). Among other things, topoisomerase I catalyzes the transient single-stranded break of a DNA double helix during DNA relaxation. Topoisomerase II catalyzes transient double-stranded breaks. Inhibition of catalytic activity of either Topo I and/or Topo H is often associated with apoptosis, thus, inhibitors of these enzymes have been targeted as useful for affecting uncontrolled cell growth and as chemotherapeutic agents.

Figure 19:
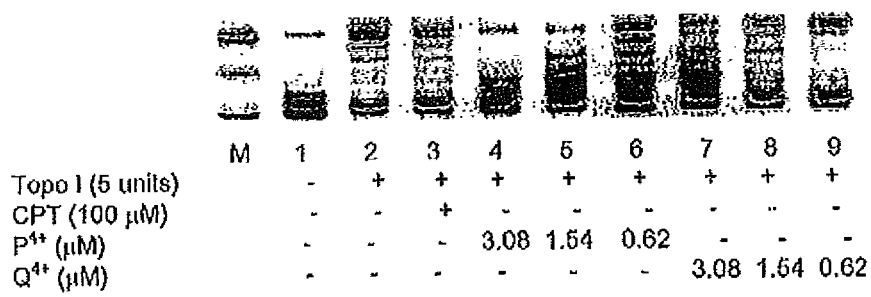
FIG. 19 depicts enzyme modifying activity for several representative compositions.
Figure 20:
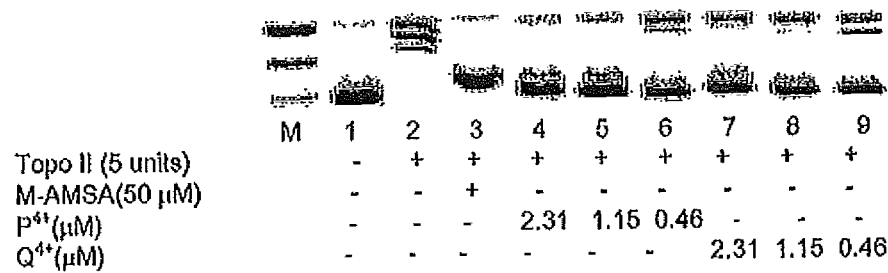
FIG. 20 depicts enzyme modifying activity for several representative compositions.

FIGS. 19 and 20 illustrate the ability of suitable compounds to modify Topo I and Topo II. For example, in FIG. 19, compounds, $P^{4+}$ and $Q^{4+}$, inhibited Topo I and its relaxation of supercoiled DNA. Inhibition by these compounds was better than that of the known inhibitor, camptothecin (CPT). For FIG. 19, lane M was the marker lane containing forms I, II and III of a DNA. For all other lanes, the DNA was supercoiled pUC18 at 30.8 µM per reaction. Lane 1 was, the DNA used was pUC18 at 30.8 µM base pairs per reaction, without compound or inhibitor. Lane 2 was DNA with Tope I and no compound. Lane 3 was DNA with inhibitor, CPT. Lane 4-6 included varying concentrations of $P^{4+}$ (3.08 µM, 1.54 µM and 0.62 µM, respectively). Lane 7-9 included varying concentrations of $Q^{4+}$ (3.08 µM, 1.54 µM and 0.62 µM, respectively).

For FIG. 20, compounds shown inhibited Topo II and its activity on supercoiled DNA. Here, inhibition was better than that of the known inhibitor, amsacrine (m-AMSA). As shown, M was the marker lane containing forms I, II and III of a DNA. For all other lanes, the DNA was supercoiled pUC18 at 30.8 µM base pairs per reaction. Lane 1 was DNA without compound or inhibitor. Lane 2 was DNA with Topo H and no compound. Lane 3 was DNA with inhibitor, m-AMSA. Lanes 4-6 included varying concentrations of $P^{4+}$ (2.31 µM, 1.15 µM and 0.46 µM, respectively). Lanes 7-9 included varying concentrations of $Q^{4+}$ (2.31 µM, 1.15 µM and 0.46 µM, respectively).

Reaction conditions for FIGS. 19 and 20 included the addition of DNA and 5 units of calf thymus Topo I in the presence or absence of either a known inhibitor (CPT), $P^{4+}$ or $Q^{4+}$. Both $P^{4+}$ and $Q^{4+}$ were examined at varying concentrations, 0.62 µM-3.08 µM. Samples were incubated at 37 degrees Centigrade in an assay buffer (e.g., 10 mM Tri-HCl at pH 7.9, 150 mM NaCl, 1 mM EDTA, 0.1% BSA, 0.1 mM spermidine, and 5% glycerol) for about 30 minutes to allow for appropriate cleavage and religation. Relaxed intermediates were then trapped by adding 5 µL of a stopping buffer (e.g., 5% SDS, 0.05% bromophenol blue and 30% glycerol). Samples were loaded on an 1% agarose gel and subjected to electrophoresis at about 5 V/cm for about 4 hours using a typical running buffer (e.g., 89 mM Tris-borate at pH 8.0, 2 mM EDTA). After electrophoresis, the gel was stained for about 30 minutes and photographed under UV light.

For conditions using Topo II, reactions were generally performed as described for Topo I, except that 23.1 µM of DNA was used per reaction along with either the inhibitor (m-AMSA) or varying concentrations of $P^{4+}$ or $Q^{4+}$ (0.46 to 2.31 µM) in a total volume of 20 µL. The assay buffer was altered for improved Topo II activity (using 10 mM Tris-HCl at pH 7.9, 50 mM NaCl, 50 mM KCl, 5 mM $MgCl_2$, 0.1 mM EDTA, 0.15 mg mL BSA, and 1 mM ATP) as was the running buffer (using 100 mM Tris-borate, pH 8.3, 2 mM BDTA).

Overall, suitable compositions exhibit modifying activity on DNA, proteins, enzymes and cells, with improved activity in hypoxic environments, such as those in which tumor cell masses exist. This later ability is critical because masses of rapidly dividing (e.g., tumorigenic cells or ones undergoing uncontrolled growth) often form as a corded structure around a functional blood vessel. In this environment, if the blood vessel is not blocked, oxygen diffusing out of the vessel is typically able to supply adequate oxygen only to those cells closest to the vessel. Tumorigenic or rapidly dividing cells further from the vessel are typically oxygen deprived and chronically hypoxic. In some cases, tumorigenic or rapidly dividing cells forming around a blood vessel become acutely hypoxic when the blood vessel supplying blood and oxygen become occluded. Accordingly, compositions described herein serve a critical role by negatively impacting and thereby reducing the number of rapidly dividing cells in hypoxic conditions as well as preventing further uncontrolled cell growth.

Such compositions display activity and toxicity that can be predicted on the basis of their bridging ligands, terminal ligands, Ru—Ru bridging distance, chirality, and redox activity. Compositions as discussed herein bind DNA, modify DNA by promoting single stranded and double stranded breaks, inhibit enzymes involved in DNA replication and division, thus, blocking DNA replication and appear to affect enzymes involved in impulse transmission. The activities are especially suited for targeting non healthy cells undergoing active, uncontrolled and rapid cell division, particularly those in hypoxic environments. Because these compositions show improved activity in low oxygen environments where non healthy cells exist and are able to present with little to no cytoxicity, they are suitable as antiproliferative, anti-cancer and/or anti-neurodegenerative drugs. In cells and animals, such compositions are cytotoxic to those cells undergoing uncontrolled cell growth, such as cancer and tumor cells and exhibits little overall toxicity to healthy, normal cells, those not undergoing uncontrolled cell growth. Accordingly, said compositions are suitable for treatment of subjects in need thereof; such subjects having cells requiring one or more antiproliferative, anti-cancer and/or anti-neurodegenerative agents.

There have been efforts to develop novel non-platinum, metal-based antitumor drugs with the aim of improving clinical effectiveness, reducing general toxicity, broadening the spectrum of activity and treating tumors which become cisplatin resistant. Much of the favorable activity attributed to cisplatin and some of the newer dinuclear platinum complexes is the slow substitutional reactivity of Pt(II) and the fact that platinum is a xenobiotic for all living things and thus cells lack the proper machinery to fully neutralize its effects. These attributes are shared by ruthenium atom complexes with their antineoplastic activity, including activity on both cisplatin resistant tumors as well as tumors on which cisplatin is inactive. Compounds also showed lower overall toxicity compared to cisplatin. These compounds may also act as pro-drugs which are hydrolyzed and reduced in vivo to an active Ru atom complex.

In the absence of oxygen, compounds described herein (e.g., $[(phen)_2Ru(tatpp)Ru(phen)_2]^{4+}$) undergoes in situ reduction by a reducing agent present in cells to form a species that causes both single strand and double strand breaks in DNA. Exposure to oxygen may attenuate the DNA modifying activity of the reduced species, even in the presence of a large excess of reducing agent (e.g., 40 equivalent GSH per compound). Accordingly, compositions may target cells in a low oxygen microenvironment for destruction. The more active species and catalytically regenerative species are identified as a reduced complex. Oxygen appears to regulate the degree to which this latter species forms and thus such species are more under hypoxic or anaerobic conditions.

The low oxygen microenvironment (hypoxia) existing in many rapidly growing solid tumors offers a mechanism is triggered to form an even more toxic species, thus capable of targeting them for destruction. Because hypoxic cells are often the most resistant to radiotherapy and chemotherapy and the most susceptible towards metastasis, compounds and compositions described herein are particularly attractive as agents for chemotherapeutic use.

Compositions as described herein are suitable as therapeutic agents by providing antiproliferative, anti-tumorigenic, anti-cancer, and/or anti-degenerative activity to name a few. Biologic modification of a DNA target provide single strand breaks and double strand breaks in close proximity as well as inhibition of: DNA replication, DNA duplication. Biologic modification of a protein or enzyme target (e.g., topoisomerase I, topoisomerase II, and those involved in impulse transmission) provide inhibition of: impulse transmission, uncontrolled cell proliferation, uncontrolled cell duplication, uncontrolled cell growth, tumor progression, and tumor growth, as examples. Compositions further exhibit improved activity under hypoxic conditions with cytotoxic activity to a biologic target under such conditions while providing little or no overall toxicity to a target not under hypoxic conditions (e.g., one or more cells undergoing uncontrolled growth). Biologic modification of such targets may be performed on a subject in need having such biologic targets requiting modification.

Compositions are also suitable for probing DNA-containing structures and/or their functions (e.g., understanding DNA intercalation and associated processes, DNA and protein footprinting, drug binding, and charge transport through DNA).

Additional objects, advantages and novel features of the invention as set forth in the description, will be apparent to one skilled in the art after reading the foregoing detailed description or may be learned by practice of the invention. The objects and advantages of the invention may be realized and attained by means of the instruments and combinations particularly pointed out here.

What is claimed is:

1. A method of modifying a cell undergoing uncontrolled cell growth comprising the steps of:
   providing a complex to the cell, wherein the complex comprises at least one ruthenium atom complexed to a first ligand that is a heterocyclic aromatic compound and to a second ligand that is redox active, wherein the second ligand comprises tatpp or tatpq and has a reduction potential that is accessible in a cellular milieu;
   reducing the redox active ligand of the complex with a reducing agent present in the cell to form a reduced complex; and
   modifying the cell with the reduced complex, wherein said modification of the cell comprises breaking one strand of DNA, breaking two strands of DNA in close proximity, inhibiting topoisomerase I, inhibiting topoisomerase II, inhibiting impulse transmission, inhibiting cell proliferation, inhibiting cell growth, inhibiting DNA replication, inhibiting DNA duplication, inhibiting tumor progression, inhibiting tumor growth, or combinations thereof, wherein said complex is active on cisplatin resistant cells that are undergoing uncontrolled cell growth, cells on which cisplatin is inactive that are undergoing uncontrolled cell growth, or both.

2. The method of claim 1, wherein the first ligand comprises pyridine, pyrimidine, ethylenediamine, 1,10-phenanthroline, 2,2'-bipyridine, or 1,10-phenanthroline-5,6-dione.

3. The method of claim 1, wherein the complex has the formula [Ru(X)$_2$tatpp]$^{2+}$ or [Ru(X)$_2$tatpq]$^{2+}$, and their salts and stereoisomers thereof, and X is a heterocyclic aromatic compound.

4. The method of claim 3, wherein X comprises pyridine, pyrimidine, ethylenediamine, 1,10-phenanthroline, 2,2'-bipyridine, or 1,10-phenanthroline-5,6-dione.

5. The method of claim 1, wherein the complex further includes a pharmaceutical carrier.

6. The method of claim 1, wherein reduction of the redox active ligand is more favorable in a hypoxic environment and the modification of the cell is enhanced.

7. The method of claim 1, wherein the reduced redox active ligand is regenerated by a cellular oxidant and is catalytic in its modification of the cell.

8. The method of claim 1, wherein the complex has the formula [Ru(phen)$_2$tatpp]$^{2+}$ or [Ru(phen)$_2$tatpq]$^{2+}$.

9. The method of claim 1, wherein the complex has the formula [Ru(phen)$_2$tatpp]$^{2+}$.

10. The method of claim 1, wherein the modification of the cell comprises breaking one strand of DNA, breaking two strands of DNA in close proximity, or a combination thereof.

11. The method of claim 1, wherein the method is performed under hypoxic conditions.

12. The method of claim 1, wherein besides the reduced complex, no additional reagent is used for the modification.

13. A method of modifying a cell undergoing uncontrolled cell growth comprising the steps of:
provide a complex to the cell, the complex having a formula selected from [Ru(X)$_2$tatpp]$^{2+}$, [Ru(X)$_2$tatpq]$^{2+}$, and salts and stereoisomers thereof, wherein tatpp and tatpq are redox active ligands and X is a heterocyclic aromatic compound, wherein tatpp or tatpq are redox active ligands that has a reduction potential that is accessible in a cellular milieu;
reducing the redox active ligand of the complex with a reducing agent present in the cell to form a reduced complex; and
modifying the cell with the reduced complex, wherein said modification of the cell comprises breaking one strand of DNA, breaking two strands of DNA in close proximity, inhibiting topoisomerase I, inhibiting topoisomerase II, inhibiting impulse transmission, inhibiting cell proliferation, inhibiting cell growth, inhibiting DNA replication, inhibiting DNA duplication, inhibiting tumor progression, inhibiting tumor growth, or combinations thereof, wherein said complex is active on cisplatin resistant cells that are undergoing uncontrolled cell growth, cells on which cisplatin is inactive that are undergoing uncontrolled cell growth, or both.

14. The method of claim 13, wherein X comprises pyridine, pyrimidine, ethylenediamine, 1,10-phenanthroline, 2,2'-bipyridine, or 1,10-phenanthroline-5,6-dione.

15. The method of claim 13, wherein the complex further includes a pharmaceutical carrier.

16. The method of claim 13, wherein the complex has the formula [Ru(phen)$_2$tatpp]$^{2+}$.

17. The method of claim 13, wherein the modification of the cell comprises breaking one strand of DNA, breaking two strands of DNA in close proximity, or a combination thereof.

18. The method of claim 13, wherein the method is performed under hypoxic conditions.

19. The method of claim 13, wherein besides the reduced complex, no additional reagent is used for the modification.

20. A method of modifying a cell undergoing uncontrolled cell growth comprising the steps of:
providing a complex to the cell, the complex having a formula selected from [Ru(phen)$_2$tatpp]$^{2+}$, [Ru(phen)$_2$tatpq]$^{2+}$, and salts and stereoisomers thereof, wherein tatpp and tatpq are redox active ligands, that has a reduction potential that is accessible in a cellular milieu;
reducing the redox active ligand of the complex with a reducing agent present in the cell to form a reduced complex; and
modifying the cell with the reduced complex, wherein said modification of the cell comprises breaking one strand of DNA, breaking two strands of DNA in close proximity, or a combination thereof, wherein the method is performed under hypoxic conditions, and wherein besides the reduced complex, no additional reagent is used for the modification.

* * * * *